United States Patent
Oishi et al.

(10) Patent No.: US 8,613,962 B2
(45) Date of Patent: Dec. 24, 2013

(54) PROPHYLACTIC OR ALLEVIATING AGENT FOR PERIPHERAL NERVE DISORDER INDUCED BY ANTI-CANCER AGENT

(75) Inventors: Ryozo Oishi, Fukuoka (JP); Yoshinori Itoh, Gifu (JP); Nobuaki Egashira, Fukuoka (JP)

(73) Assignees: Kyushu University, National University Corporation, Fukuoka (JP); Nippon Zoki Pharmaceutical Co., Ltd, Osaka (JP)

( * ) Notice: Subject to any disclaimer, the term of this patent is extended or adjusted under 35 U.S.C. 154(b) by 744 days.

(21) Appl. No.: 12/674,972

(22) PCT Filed: Aug. 28, 2008

(86) PCT No.: PCT/JP2008/065399
§ 371 (c)(1),
(2), (4) Date: Mar. 25, 2010

(87) PCT Pub. No.: WO2009/028605
PCT Pub. Date: Mar. 5, 2009

(65) Prior Publication Data
US 2011/0111051 A1  May 12, 2011

(30) Foreign Application Priority Data

Aug. 31, 2007 (JP) ................. 2007-225420
Feb. 14, 2008 (JP) ................. 2008-032626

(51) Int. Cl.
| A61K 35/00 | (2006.01) |
| A61K 35/12 | (2006.01) |
| A01N 63/00 | (2006.01) |
| A01N 63/02 | (2006.01) |
| A01N 65/00 | (2009.01) |

(52) U.S. Cl.
USPC ........ 424/780; 424/93.1; 424/93.6; 424/93.7; 424/520; 424/572

(58) Field of Classification Search
None
See application file for complete search history.

(56) References Cited

U.S. PATENT DOCUMENTS

| 5,013,558 | A | 5/1991 | Konishi |
| 5,560,935 | A | 10/1996 | Konishi et al. |
| 6,051,613 | A | 4/2000 | Ohno et al. |
| 6,165,515 | A | 12/2000 | Matsuyama et al. |
| 2001/0044465 | A1 | 11/2001 | Cavazza et al. |
| 2003/0199535 | A1 | 10/2003 | Cavazza et al. |
| 2003/0203960 | A1 | 10/2003 | Hausheer |
| 2006/0051376 | A1 | 3/2006 | Nishioka |
| 2006/0183798 | A1 | 8/2006 | Cavazza et al. |
| 2006/0258744 | A1 | 11/2006 | Cavazza et al. |
| 2006/0263388 | A1 | 11/2006 | Nishioka |
| 2007/0218037 | A1 | 9/2007 | Nishioka |
| 2008/0194683 | A1 | 8/2008 | Cavazza et al. |
| 2009/0137619 | A1 | 5/2009 | Cavazza et al. |
| 2009/0143464 | A1 | 6/2009 | Cavazza et al. |

FOREIGN PATENT DOCUMENTS

| JP | 53-101515 | 9/1978 |
| JP | 55-087724 | 7/1980 |
| JP | 1-265028 | 10/1989 |
| JP | 1-319422 | 12/1989 |
| JP | 2-28119 A | 1/1990 |
| JP | 7-097336 | 4/1995 |
| JP | 8-291077 | 11/1996 |
| JP | 10-194978 | 7/1998 |
| JP | 11-080005 | 3/1999 |
| JP | 11-139977 | 5/1999 |
| JP | 2000-16942 A | 1/2000 |
| JP | 2000-336034 | 12/2000 |
| JP | 2004-300146 | 10/2004 |
| JP | 2005-525409 | 8/2005 |
| JP | 2006-508958 | 3/2006 |
| WO | WO2004/039383 A1 | 5/2004 |

OTHER PUBLICATIONS

Kawashiri, Takehiro et al: "Neurotropin reverses paclitaxel-induced neuropathy without affecting anti-tumour efficacy", European Journal of Cancer, Pergamon Press, Oxford GB vol. 45, No. 1, pp. 154-163, (2009) (Available online Nov. 20, 2008).

European Search report for EP application No. 08828811 dated, Feb. 28, 2011.

Zhang Ming-zhi et al., "A Clinical study of Neurotropin in the treatment of peripheral nervous caused by CHOP regimen in the NHL patient", Journal of Leukemia & Lymphoma, vol. 16, No. 3, Jun. 30, 2007, pp. 190-191 and English translation thereof.

Gong Xiao-xia et al., "The clinical observation on precaution of oxaliplatin peripheral nerve oxaliplatin toxicity using buyang huanwu decoction", HeNan traditional Chinese Medicine, vol. 25, No. 11, Nov. 30, 2005, pp. 68 and English translation thereof.

Ruksal et al, "Effects of Neurotropin on Hyperalgesia and Allodynia in Mononeuropathic Rats," Life Sciences, 1998, vol. 63, No. 21, pp. 1931-1938.

China Office action, dated May 24, 2013 along with an English translation thereof.

Japan Office action, dated May 22, 2013.

*Primary Examiner* — Debbie K Ware

(74) *Attorney, Agent, or Firm* — Greenblum & Bernstein, P.L.C.

(57) ABSTRACT

There is provided a medicinal agent that is effective and highly safe for the prevention or alleviation of a peripheral nerve disorder that develops as a side effect occurring after the administration of an anti-cancer agent. The present invention relates to a novel medical use of an extract from inflamed tissues inoculated with vaccinia virus, and to a prophylactic or alleviating agent for a peripheral nerve disorder that contains the extract as an active ingredient. The agent containing the extract as an active ingredient is used for a prophylactic or alleviating agent for a peripheral nerve disorder induced by an anti-cancer agent and is a highly safe and remarkably highly useful medicinal agent with few side effects.

26 Claims, 5 Drawing Sheets

\*: P<0.05, \*\*: P<0.01 vs. GROUP ADMINISTERED WITH OXALIPLATIN

\*: P<0.05 vs. GROUP ADMINISTERED WITH OXALIPLATIN

US 8,613,962 B2

PROPHYLACTIC OR ALLEVIATING AGENT FOR PERIPHERAL NERVE DISORDER INDUCED BY ANTI-CANCER AGENT

TECHNICAL FIELD

The present invention relates to a novel medical use of an extract from inflamed tissues inoculated with vaccinia virus, and in particular, relates to a prophylactic or alleviating agent for a peripheral nerve disorder induced by an anti-cancer agent that contains, as an active ingredient, an extract from inflamed tissues inoculated with vaccinia virus.

BACKGROUND ART

In current cancer (malignant tumor) treatment, surgery, irradiation or chemotherapy is used alone or in any combination thereof as required. Among them, anti-cancer agents (anti-malignant-tumor agents) used in the chemotherapy inherently have cytotoxicity or cell inhibition and damage not only the cancer (malignant tumor) cells but also human normal cells to cause side effects. Thus, it is important that the anti-cancer agents are administered to patients so as to prevent or reduce such side effects as far as possible and to provide sufficient anti-cancer (anti-malignant-tumor) effects.

Examples of the side effects caused by the administration of anti-cancer agents include blood disorders, gastrointestinal disorders and nerve disorders, and, in particular, acute or chronic nerve disorders have increased as a recent trend. This trend is considered to be caused by the following factors: frequent occurrence of nerve disorders as a main side effect of new anti-cancer agents providing remarkable anti-cancer effects, the effects of multiple drug therapy as recent main therapy, and an improving tendency of side effects such as blood disorders and gastrointestinal disorders. In this manner, no effective countermeasures against the nerve disorders, which are a main side effect caused by the current cancer chemotherapy, are available once the disorders have developed, due to the difficulty of nerve cell regeneration. Therefore, serious symptoms or irreversible disorders may be caused because of the difficulty of nerve cell regeneration. Accordingly, the nerve disorders that are the main side effect are an important therapeutic problem.

The nerve disorders caused by the administration of anti-cancer agents are observed in, besides the central nervous system, the autonomic nervous system, and the peripheral nervous system, the sense organs such as the sense of taste. Among them, nerve disorders that occur in a comparatively high frequency to be problems are pains such as a stinging pain and burning pain, paresthesia such as numbness of limb extremities and a burning sensation, hyperesthesia such as hypersensitivity to cold stimuli, dysesthesia such as sensory loss, sensory paralysis and sense of discomfort, and nerve disorders in the peripheral nervous system such as sensory ataxia and muscle weakness. The lesions in the peripheral nervous system induced by the administration of anti-cancer agents are considered mainly due to axonal degeneration. Microtubules in the axon play an important role in maintaining the normal function of cells, for example, forming a spindle during cell division, placing the subcellular organelle and transporting substances. Taxane drugs such as paclitaxel and docetaxel and vinca alkaloid drugs such as vincristine, vinblastine, vindesine and vinorelbine target the microtubules to inhibit the proliferation of malignant tumor cells. Thus, it is considered that the microtubules in normal nerve cells are also damaged to cause the nerve disorders. Furthermore, it is considered that platinum drugs such as oxaliplatin, carboplatin, cisplatin and nedaplatin directly damage nerve cells and consequently axonopathy is secondarily caused.

However, the neurotoxicity of the anti-cancer agents has not been studied in detail and preventive and supportive methods for the nerve disorders have yet to be established. Therefore, for relieving numbness symptoms, vitamin preparations such as mecobalamin and a Chinese herbal medicine, Goshajinki-gan, are used. For pains, an antidepressant (amitriptyline hydrochloride), an antiepileptic agent (carbamazepine), an antiarrhythmic agent (mexiletine hydrochloride), adrenocorticosteroid and the like are used. However, the radical treatment or prophylaxis has yet to be established. Accordingly, stopping/reducing the administration of a medicinal agent is the only reliable method for preventing the development of the nerve disorders (however, even after stopping the administration, the nerve disorders may continue or get worse). In view of the above problems, prophylactic or alleviating agents effective against a nerve disorder induced by anti-cancer agents have been strongly required in clinical practices.

The extract from inflamed tissues inoculated with vaccinia virus as an active ingredient in the medicinal agent of the present invention is disclosed to have the following effects: an analgesic effect, sedative effect, anti-stress effect and anti-allergic effect (see Patent Document 1); an immunostimulating effect, anti-cancer effect and cirrhosis inhibitory effect (see Patent Document 2); a treatment effect against idiopathic thrombocytopenic purpura (see Patent Document 3); a treatment effect against postherpetic neuralgia, brain edema, dementia, spinocerebellar degeneration and the like (see Patent Document 4); a treatment effect against Raynaud syndrome, diabetic neuropathy, sequelae of subacute myelo-optico-neuropathy and the like (see Patent Document 5); a kallikrein production inhibitory effect and peripheral circulatory disorder improving effect (see Patent Document 6); a bone atrophy improving effect (see Patent Document 7); a nitric oxide production inhibitory effect effective for the treatment of sepsis and endotoxic shock (see Patent Document 8); a treatment effect against osteoporosis (see Patent Document 9); a treatment effect against AIDS based on a Nef action inhibitory effect and chemokine production inhibitory effect (Patent Documents 10 and 11); a treatment effect against ischemic disorders such as cerebral infarction (Patent Document 12); a treatment effect against fibromyalgia syndrome (Patent Document 13); and a treatment effect against infections (Patent Document 14) and the like.

In particular, Patent Document 5 describes that the extract from inflamed tissues inoculated with vaccinia virus as an active ingredient in the medicinal agent of the present invention improves symptoms such as numbness, pain, coldness of limbs and paresthesia that are caused by the dysfunction of ischemic tissues or organs due to local blood circulation disorders of living organisms. However, the improving effect on numbness, pain, coldness of limbs, paresthesia and the like by the extract from inflamed tissues inoculated with vaccinia virus disclosed in Patent Document 5 is an effect based on the bloodstream improving effect on an ischemic condition due to blood circulation disorders. By contrast, such a prevention or alleviation effect in the present invention on the peripheral nerve disorders as the side effect (cellular damage) induced by the administration of anti-cancer agents is the effect of the extract on the peripheral nerve disorders having entirely different developing mechanisms and is unknown findings. That is, it is not known that the extract is effective for, for example, alleviation of peripheral nerve disorders that are considered to be caused by the damage of microtubules of nerve axons, demyelination of nerve axons, direct damage to nerve cells and the like induced by the administration of anti-cancer agents, and such medical use has not been published and reported yet.

[Patent Document 1]
Japanese Patent Application Publication No. JP-A-53-101515
[Patent Document 2]
Japanese Patent Application Publication No. JP-A-55-87724 (pages 3, 5 and 6)
[Patent Document 3]
Japanese Patent Application Publication No. JP-A-1-265028 (pages 1 and 2)
[Patent Document 4]
Japanese Patent Application Publication No. JP-A-1-319422 (pages 3 and 4)
[Patent Document 5]
Japanese Patent Application Publication No. JP-A-2-28119 (page 3)
[Patent Document 6]
Japanese Patent Application Publication No. JP-A-7-97336 (page 4)
[Patent Document 7]
Japanese Patent Application Publication No. JP-A-8-291077
[Patent Document 8]
Japanese Patent Application Publication No. JP-A-10-194978
[Patent Document 9]
Japanese Patent Application Publication No. JP-A-11-80005 (pages 2 and 3)
[Patent Document 10]
Japanese Patent Application Publication No. JP-A-11-139977
[Patent Document 11]
Japanese Patent Application Publication No. JP-A-2000-336034 (pages 2 and 3)
[Patent Document 12]
Japanese Patent Application Publication No. JP-A-2000-16942
[Patent Document 13]
International Publication No. WO 2004/039383
[Patent Document 14]
Japanese Patent Application Publication No. JP-A-2004-300146

DISCLOSURE OF THE INVENTION

Problem to be Solved by the Invention

It is an object of the present invention to provide a medicinal agent that is effective and highly safe for the prevention or alleviation of a peripheral nerve disorder that develops as a side effect occurring after the administration of an anti-cancer agent.

Means for Solving the Problem

The inventors of the present invention have carried out intensive studies, and as a result, have found that an extract from an inflamed tissue inoculated with vaccinia virus provides an excellent prevention or alleviation effect on a peripheral nerve disorder induced by an anti-cancer agent, and the present invention has been accomplished.

Effects of the Invention

The extract from an inflamed tissue inoculated with vaccinia virus has excellent pharmacological effects of preventing or alleviating the peripheral nerve disorder induced by the administration of an anti-cancer agent. Furthermore, the medicinal agent of the present invention containing the extract as an active ingredient has fewer problems such as side effects and is safe and highly useful.

BEST MODES FOR CARRYING OUT THE INVENTION

Figure 1:
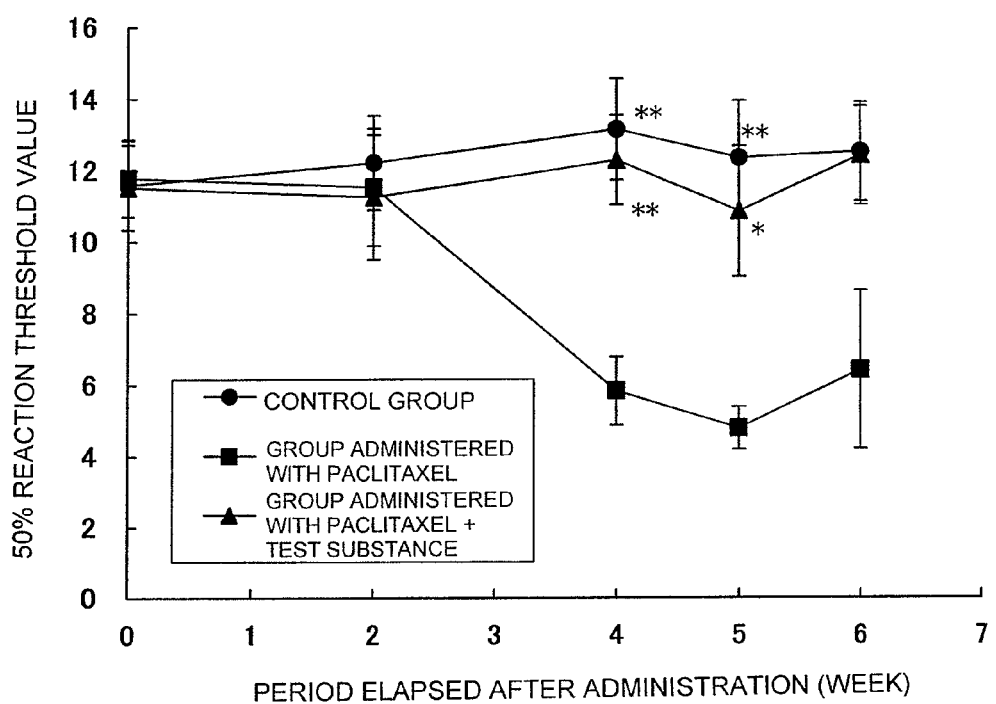
FIG. 1 is an experimental result of the von Frey test on alleviation effect of an extract from inflamed tissues inoculated with vaccinia virus of the present invention on the hyperesthesia induced by the administration of paclitaxel.

The present invention relates to a prophylactic or alleviating agent for a peripheral nerve disorder induced by an anti-cancer agent containing, as an active ingredient, an extract from an inflamed tissue inoculated with vaccinia virus. The anti-cancer agent developing the peripheral nerve disorder in the present invention is an anti-cancer agent that specifically damages microtubules to induce the peripheral nerve disorder. Examples of such medicinal agent include taxane drugs such as paclitaxel and docetaxel and vinca alkaloid drugs such as vincristine, vinblastine, vindesine and vinorelbine. In addition, examples of the medicinal agent that damages nerve cells to cause axonopathy and then induces the peripheral nerve disorder include platinum drugs such as oxaliplatin, carboplatin, cisplatin and nedaplatin. Examples of the peripheral nerve disorder induced by these anti-cancer agents include pain, numbness, paresthesia, dysesthesia and hyperesthesia. Because of the disorder, impairment such as ataxia, for example, difficulty in holding an object, difficulty in fastening buttons and gait disturbance, or reduction of deep tendon reflex occurs in daily life. The peripheral nerve disorder induced by an anti-cancer agent that the medicinal agent of the present invention is intended to prevent or improve includes a peripheral nerve disorder induced by monotherapy using one type of anti-cancer agent as well as a peripheral nerve disorder induced by multiple drug therapy in which a plurality of medicinal agents having various action mechanisms is administered or by biochemical modulation in which a combination of medicinal agents and an administration method are designed such that the medicinal agents having various action mechanisms can provide the maximum effectiveness.

As for the extract from inflamed tissues inoculated with vaccinia virus used in the medicinal agent of the present invention, there are various reports on physiological active substances produced in the inflamed tissues inoculated with vaccinia virus, the method for extracting the substances from the diseased tissues, the pharmacological activities and the like as mentioned above (for example, Patent Documents 1 to 14).

Furthermore, a preparation of an extract from inflamed skins of rabbits inoculated with vaccinia virus is a commercially available pharmaceutical product. The preparation, as described in pages 2697 to 2699 of "Drugs in Japan, Ethical Drugs" (2007, edited and published by Japan Pharmaceutical Information Center), is a medicinal agent containing non-proteinous active substances extracted and separated from the inflamed skin tissues of rabbits inoculated with vaccinia virus. The preparation is known to be effective against low back pain, cervicobrachial syndrome, symptomatic neuralgia, periarthritis scapulohumeralis, osteoarthritis, itchiness accompanied with skin diseases (eczema, dermatitis, urticaria), allergic rhinitis, sequelae of subacute myelo-optico-neuropathy such as coldness, paresthesia and pain, postherpetic neuralgia and the like. The preparation is approved as an ethical drug in the form of hypodermic, intramuscular and intravenous injection products and of tablets and is commercially available.

The extract from inflamed tissues inoculated with vaccinia virus used in the medicinal agent of the present invention is a non-proteinous biofunction-regulating substance extracted from the inflamed tissues inoculated with vaccinia virus as described above, and the preparation of the extracted solution from inflamed skins of rabbits inoculated with vaccinia virus listed in the "Drugs in Japan, Ethical Drugs" is approved as a pharmaceutical product and is commercially available. In addition, various extracts from inflamed tissues inoculated with vaccinia virus described in Patent Documents described above may be used as the substance of the present invention, and their producing methods, suitable doses and the like are also given in the documents.

The extract from inflamed tissues inoculated with vaccinia virus used in the medicinal agent of the present invention can be obtained by the following manner: inflamed tissues inflamed by the inoculation with vaccinia virus is crushed; an extraction solvent is added to remove the tissue fragments; then deproteinization is carried out; the deproteinized solution is adsorbed onto an adsorbent; and then the active ingredient is eluted.

The extract from inflamed tissues inoculated with vaccinia virus is produced, for example, according to the following process.

(a) Inflamed skin tissues of rabbits, mice or the like by the inoculation with vaccinia virus are collected, and the inflamed tissues are crushed. To the crushed tissue an extraction solvent such as water, phenolated water, physiological saline or phenol-added glycerin water is added. Then, the mixture is filtered or centrifuged to obtain an extraction liquid (filtrate or supernatant).

(b) The pH of the extraction liquid is adjusted to be acidic and the liquid is heated for deproteinization. Then, the deproteinized solution is adjusted to be alkaline, heated, and then filtered or centrifuged.

(c) The obtained filtrate or supernatant is made acidic and adsorbed onto an adsorbent such as activated carbon or kaolin.

(d) To the adsorbent, an extraction solvent such as water is added, the pH is adjusted to alkaline, and the adsorbed component is eluted to obtain the extract from inflamed tissues inoculated with vaccinia virus. Subsequently, as desired, the eluate may be evaporated to dryness under reduced pressure or freeze-dried to give a dried material.

As for animals in order to obtain the inflamed tissues by the inoculation of vaccinia virus, various animals that is infected with vaccinia virus such as rabbits, cows, horses, sheep, goats, monkeys, rats or mice can be used, and preferred inflamed tissues are inflamed skin tissues of rabbits.

The inflamed tissues are collected and crushed, and 1 to 5 volumes of extraction solvent is added to make an emulsified suspension. As for the extraction solvent, distilled water, physiological saline, weakly acidic to weakly basic buffer and the like can be used, and stabilizers such as glycerin, antibacterial/antiseptic agents such as phenol, and salts such as sodium chloride, potassium chloride or magnesium chloride may be suitably added. At this time, the extraction may be facilitated by breaking the cellular tissues with treatment such as freezing and thawing, ultrasonic waves, cell membrane dissolving enzymes or surfactants.

The obtained emulsified extraction liquid is subjected to filtration, centrifugation or the like to remove tissue fragments, and then deproteinized. The deproteinization operation may be carried out by a generally known method, for example, heat treatment, treatment with a protein denaturant such as an acid, base, urea and guanidine, treatment with an organic solvent such as acetone, isoelectric precipitation, and salting out can be applied. Then, by a general method for removing insolubles such as filtration using filter paper (for example, cellulose or nitrocellulose), glass filters, Celite, Seitz filters or the like, ultrafiltration and centrifugation, the precipitated insoluble protein is removed.

The extraction liquid containing active ingredients obtained in this manner is acidified, preferably adjusted to pH 3.5 to 5.5 with an acid such as hydrochloric acid, sulfuric acid or hydrobromic acid, and then adsorbed onto an adsorbent. Examples of the usable adsorbent include activated carbon and kaolin. The adsorbent may be added into the extraction liquid to stir, or the extraction liquid may be passed through a column filled with the adsorbent to adsorb the active ingredients onto the adsorbent. When the adsorbent is added into the extraction liquid, the solution is removed by filtration, centrifugation, or the like to obtain the adsorbent in which the active ingredients are adsorbed.

In order to elute (desorb) the active ingredients from the adsorbent, an elution solvent is added to the adsorbent to elute at room temperature or with suitable heating or with stirring, and the adsorbent is removed by a general method such as filtration, centrifugation, or the like. As for the elution solvent to be used, a basic solvent such as water, methanol, ethanol or isopropanol that are adjusted to have a basic pH or a suitable mixture thereof may be used, and preferably water adjusted to pH 9 to 12 may be used.

The extract (eluate) obtained in this manner may be properly prepared in a suitable form as a raw material for a formulation or a pharmaceutical formulation. For example, the solution may be adjusted to have nearly neutral pH to be a raw material for a formulation, and may be adjusted to have a desired concentration by concentration or dilution. In addition, for a formulation for injection, sodium chloride may be added to prepare a solution isotonic to physiological saline. Furthermore, the solution may be concentrated to dryness or freeze-dried to prepare a solid form available for the raw material of tablets or the like.

Examples of an administration method to a patient include oral and other administrations such as subcutaneous, intramuscular and intravenous administrations. The dose can be suitably determined depending on the type of extract from inflamed tissues inoculated with vaccinia virus. The dose that is approved in the commercially available preparation according to the "Drugs in Japan, Ethical Drugs" (page 2499) is principally 16 NU per day by oral administration and 3.6 to 7.2 NU per day by injection as an ethical drug. However, the dose may be appropriately increased or decreased depending on the type of disease, degree of seriousness, individual difference in the patients, method of administration, period of administration and the like (NU: Neurotropin unit. Neurotropin unit is defined by $ED_{50}$ value of analgesic effect measured by a modified Randall-Selitto method using SART-stressed mice that are chronic stressed animals showing a lowered pain threshold than normal animals. One NU indicates the activity of 1 mg of analgesic ingredients in Neurotropin preparations when the $ED_{50}$ value is 100 mg/kg of the preparation).

Hereinafter, examples of methods for producing an extract from inflamed tissues inoculated with vaccinia virus as well as results of a pharmacological test concerning novel pharmacological activity of the extract, that is, prevention or alleviation effect of the nerve disorder induced by anti-cancer agents, are described.

The present invention is not intended to be limited to the descriptions in Examples.

EXAMPLES

Example 1

Skins of healthy adult rabbits were inoculated with vaccinia virus. The inflamed skins were removed and crushed, and to the crushed skins, phenolated water was added. Then, the mixture was filtered under pressure, and the obtained filtrate was adjusted to pH 5 with hydrochloric acid, and then heated at 90 to 100° C. for 30 minutes. After deproteinization by filtration, the filtrate was adjusted to pH 9 with sodium hydroxide, further heated at 90 to 100° C. for 15 minutes, and then filtered. The filtrate was adjusted to about pH 4.5 with hydrochloric acid, and 2% activated carbon was added. The mixture was stirred for 2 hours and then centrifuged. To the collected activated carbon, water was added. The mixture was adjusted to pH 10 with sodium hydroxide, stirred at 60° C. for 1.5 hours, and then centrifuged and filtered to obtain a supernatant. To the collected activated carbon, water was added again. The mixture was adjusted to pH 11 with sodium hydroxide, stirred at 60° C. for 1.5 hours, and then centrifuged to obtain a supernatant. The two supernatants were combined and neutralized with hydrochloric acid to obtain an extract from inflamed skins of rabbits inoculated with vaccinia virus. In the following pharmacological tests, the extract was adjusted to an appropriate concentration to be used.

Example 2

Skins of healthy adult rabbits were inoculated with vaccinia virus to be infected. Subsequently, the inflamed skins were aseptically removed and chopped, and then phenol-added glycerin water was added. The mixture was ground with a homogenizer to be emulsified. Subsequently, the emulsion was filtered. The obtained filtrate was adjusted to weak acidity (pH 4.5 to 5.5) with hydrochloric acid, then heated at 100° C. and filtered. The filtrate was adjusted to weak alkalinity (pH 8.5 to 10.0) with sodium hydroxide, further heated at 100° C. and then filtered. The filtrate was adjusted to about pH 4.5 with hydrochloric acid, and about 1.5% activated carbon was added. The mixture was stirred for 1 to 5 hours and then filtered. To the activated carbon collected by the filtration, water was added. The mixture was adjusted to pH 9.4 to 10 with sodium hydroxide, stirred for 3 to 5 hours, and then filtered. The filtrate was neutralized with hydrochloric acid.

Example 3

Skins of healthy adult rabbits were inoculated with vaccinia virus to be activated. Then the activated skins were aseptically removed and chopped, and water was added. The mixture was ground with a homogenizer to be emulsified. Subsequently, the emulsion was filtered under pressure. The obtained filtrate was adjusted to pH 5.0 with hydrochloric acid, and then heated at 100° C. with flowing steam. After deproteinization by filtration, the filtrate was adjusted to pH 9.1 with sodium hydroxide, further heated at 100° C. and then filtered. The filtrate was adjusted to pH 4.1 with hydrochloric acid, and 2% activated carbon was added. The mixture was stirred for 2 hours and then filtered. To the filtrate, 5.5% activated carbon was further added, and the mixture was stirred for 2 hours and then filtered. To the activated carbon collected by the former filtration, water was added. The mixture was adjusted to pH 9.9 with sodium hydroxide, stirred at 60° C. for 1.5 hours, and then filtered. To the former activated carbon and the latter activated carbon, water was added. The mixture was adjusted to pH 10.9 with sodium hydroxide, stirred at 60° C. for 1.5 hours, and then filtered. The filtrates were combined and neutralized with hydrochloric acid. Then, the filtrate was desalted by electrodialysis using a membrane with a molecular weight of 100, and dried under reduced pressure.

Next, an example of the pharmacological test results concerning alleviation effect on nerve disorders induced by anti-cancer agents in which the extract from inflamed tissues inoculated with vaccinia virus of the present invention obtained in Example 1 was used as a test substance, is shown. Here, in all pharmacological tests, the Tukey-Kramer method was used for a significance test.

Pharmacological Test 1

Effect on Rat Peripheral Nerve Disorder Induced by Paclitaxel

The effect of the extract of the present invention (the extract from inflamed skins of rabbits inoculated with vaccinia virus produced in Example 1) was examined on hyperesthesia such as allodynia (severe pain induced by tactile stimuli that usually cause no pain) by mechanical stimuli and on paresthesia in low temperature stimuli induced by the administration of paclitaxel, an anti-cancer agent. The extract of the present invention was orally administered to rats as a test substance, and the following experiments (von Frey test and acetone test) were carried out.

(1) Administration of Test Substance 7 and 8-week-old SD male rats were used as experimental animals and separated into three groups of a control group, group administered with paclitaxel, and group administered with paclitaxel and the test substance (group administered with paclitaxel+test substance). To the group administered with paclitaxel, paclitaxel (6 mg/kg) was intraperitoneally administered once a week for 4 weeks in a total of 4 times. To the group administered with paclitaxel+test substance, the test substance (200 NU/kg) was orally administered three times a week, that is, just before the paclitaxel administration and on days 1 and 2 after the paclitaxel administration, for 4 weeks in a total of 12 times. To the control group, a solvent (polyoxyethylene castor oil:ethanol=1:1) used in the paclitaxel administration was similarly administered.

(2) von Frey Test

Each of the rats in three groups of (1) was placed in a cage with a wire-meshed bottom, and acclimated for 1 hour. Subsequently, a von Frey filament with a bending force of 2, 4, 6, 8, 10 or 15 g was vertically pressed with respect to the posterior plantar until the filament was bent, and the pressure was kept for 6 seconds. This operation was repeated 6 times for each of the right and left posterior plantars to count the avoidance reactions. The measurement was performed after 0, 2, 4, 5 and 6 weeks of the administration starting. A scatter diagram where the bending force of filament (g) was x and the number of avoidance reactions was y was prepared. Then, based on the sigmoid curve of $y=A/(1+(\exp(-B \times (x-C)))$ obtained by the method of least squares, the bending force of filament corresponding to 6 reactions (50%) was calculated as a 50% reaction threshold value to evaluate the effect of the test substance on allodynia.

An example of the test results is shown in FIG. 1. In the group administered with paclitaxel, the 50% reaction threshold value is remarkably lowered as compared with that in the control group. In the group administered with paclitaxel+test substance in which paclitaxel was administered in combination with the extract of the present invention, substantially the same 50% reaction threshold value was shown as in the control group, and lowering the 50% reaction threshold value was significantly inhibited in comparison with the group administered with paclitaxel. Furthermore, in the group administered with paclitaxel+test substance, it was revealed that the pain threshold value lowering continued to be inhibited even after the completion of the administration of the test substance. From the above results, the extract of the present invention was ascertained to have excellent prevention or improvement effect on the hyperesthesia induced by paclitaxel.

(3) Acetone Test

Each of the rats in three groups of (1) was placed in a cage with a wire-meshed bottom and acclimated for 1 hour. Then, 50 μL of acetone was sprayed to the posterior foot over for 5 seconds using a MicroSprayer (manufactured by Penn-Century, Inc.) to provide cold stimuli by utilizing the cooling effect during acetone vaporization. The avoidance reaction of the rat was observed for 40 seconds from the start of spraying, and time to the reaction (latent time) was recorded. The test was repeated three times for each of the right and left feet, and the mean value was calculated.

Figure 2:
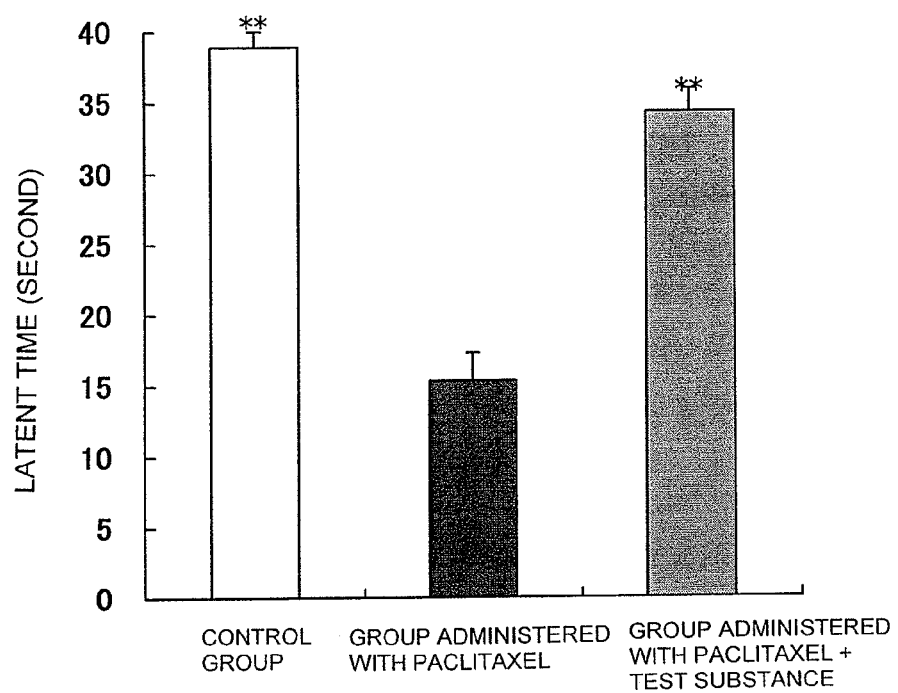
FIG. 2 is an experimental result of the acetone test on alleviation effect of the extract from inflamed tissues inoculated with vaccinia virus of the present invention on the paresthesia induced by the administration of paclitaxel.

An example of the test results is shown in FIG. 2. With respect to the cold stimuli with acetone, in the group administered with paclitaxel, the latent time was remarkably shortened, but in the group administered with paclitaxel+test substance, the latent time was recovered substantially the same level as in the control group. From the results, the extract of the present invention was ascertained to have an excellent effect on paresthesia (hypersensitivity to cold stimuli) induced by paclitaxel. By contrast, in the test with heat stimuli (plantar test), the latent time was not shortened by the administration of paclitaxel, and also in the group administered with paclitaxel+test substance, the latent time was almost the same as in the control group and the group administered with paclitaxel. Examples of the characteristic symptom of a peripheral nerve disorder induced by anti-cancer agents include hypersensitivity with respect to cold stimuli. The test (acetone test) reflects the symptom, and thus the result shows an excellent prevention or improvement effect of the extract of the present invention on the hyperesthesia caused by anti-cancer agents.

Pharmacological Test 2

Effect on Nerve Cell Denaturation Induced by Paclitaxel in In Vitro Test System

In order to examine pharmacological effect of the extract of the present invention on nerve cell denaturation induced by the treatment of paclitaxel, an anti-cancer agent, using rat pheochromocytoma 12 (PC12) cells and dorsal root ganglia (DRG) cells that are model cell lines for neuronal differentiation and neurite outgrowth, the following experiments were carried out.

(1) Cell Culturing

PC12 cells were cultured in an 80 cm$^3$ flask using RPMI 1640 medium (manufactured by MP Biomedicals, LLC) containing 5% fetal bovine serum, 10% horse serum and 100 unit/ml penicillin-streptomycin (manufactured by Gibco BRL) at 37° C. in a 5% $CO_2$ incubator.

Apart from the above, DRG cells from male Sprague-Dawley rats were primary cultured, and then five nodes of L4-5 DRG were treated with collagenase type I (manufactured by Funakoshi Corporation) and dispase I (manufactured by Sanko Junyaku Co., Ltd), then seeded into a 24-well plate and cultured. The cultivation was carried out using Dulbecco's modified Eagle's medium (DMEM medium, manufactured by MP Biomedicals, LLC) containing 10% fetal bovine serum and 100 unit/ml penicillin-streptomycin (manufactured by Gibco BRL) at 37° C. in a 5% $CO_2$ incubator.

(2) Drug Treatment and Neurite Length Measurement of Drug

The PC12 cells were seeded into a 24-well plate at 10,000 cell/well, and after 3 hours, treated with 10 μM forskolin to induce neurite outgrowth. After 24 hours, drug treatment was carried out. On the other hand, the DRG cells were cultured for a week, the cell adhesion and neurite outgrowth were checked, and then drug treatment was carried out. The drug treatment was carried out with a drug using 10 ng/mL paclitaxel only and a drug using a combination of 10 ng/mL paclitaxel and the test substance having each concentration (0.001, 0.003, 0.01 or 0.03 NU/mL). After 24 and 96 hours of the drug treatment, the medium was replaced with a new culture medium containing the drug and the test substance each having a predetermined concentration. After 168 hours, dead cells were distinguished by being colored with a trypan blue stain, and optical photomicrographs were taken (×200, 3 fields of view/well). After taking the images, using analysis software Image J, the length of neurite in the living cells was measured.

Figure 3:
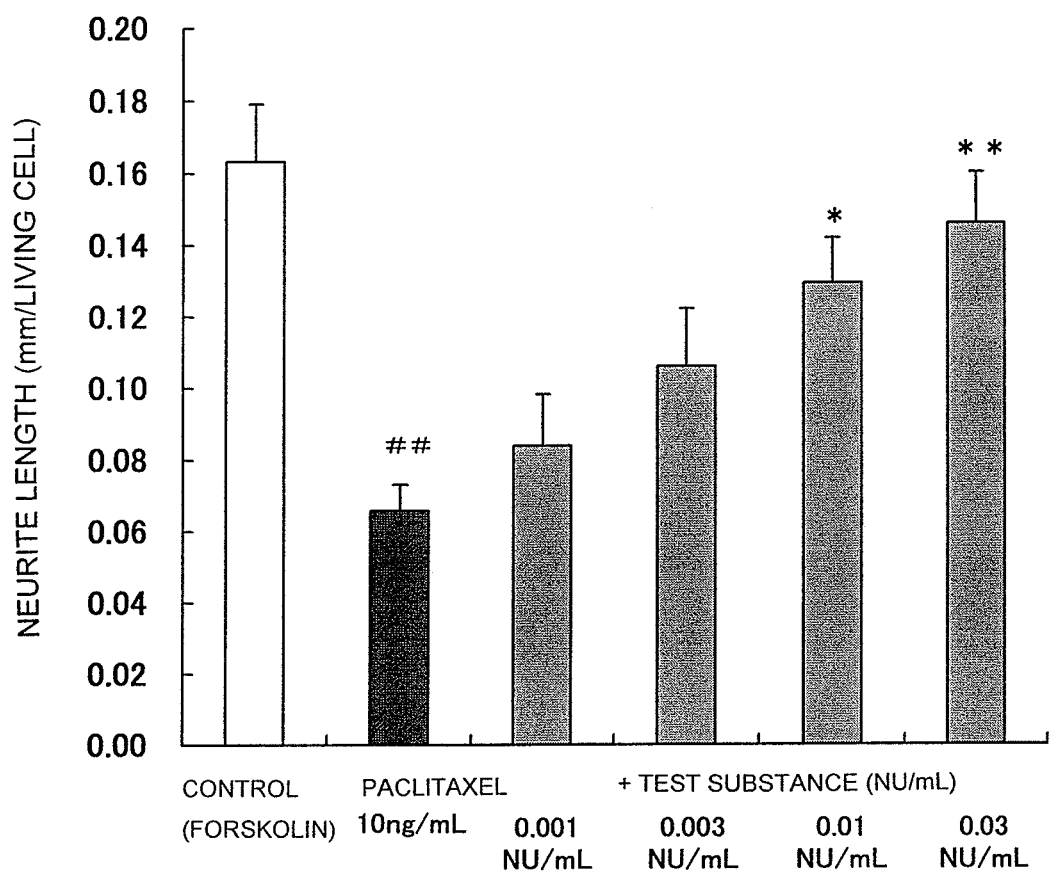
FIG. 3 is an experimental result using PC12 cells on suppressive effect of the extract from inflamed tissues inoculated with vaccinia virus of the present invention on the neurite outgrowth inhibition induced by paclitaxel.
Figure 4:
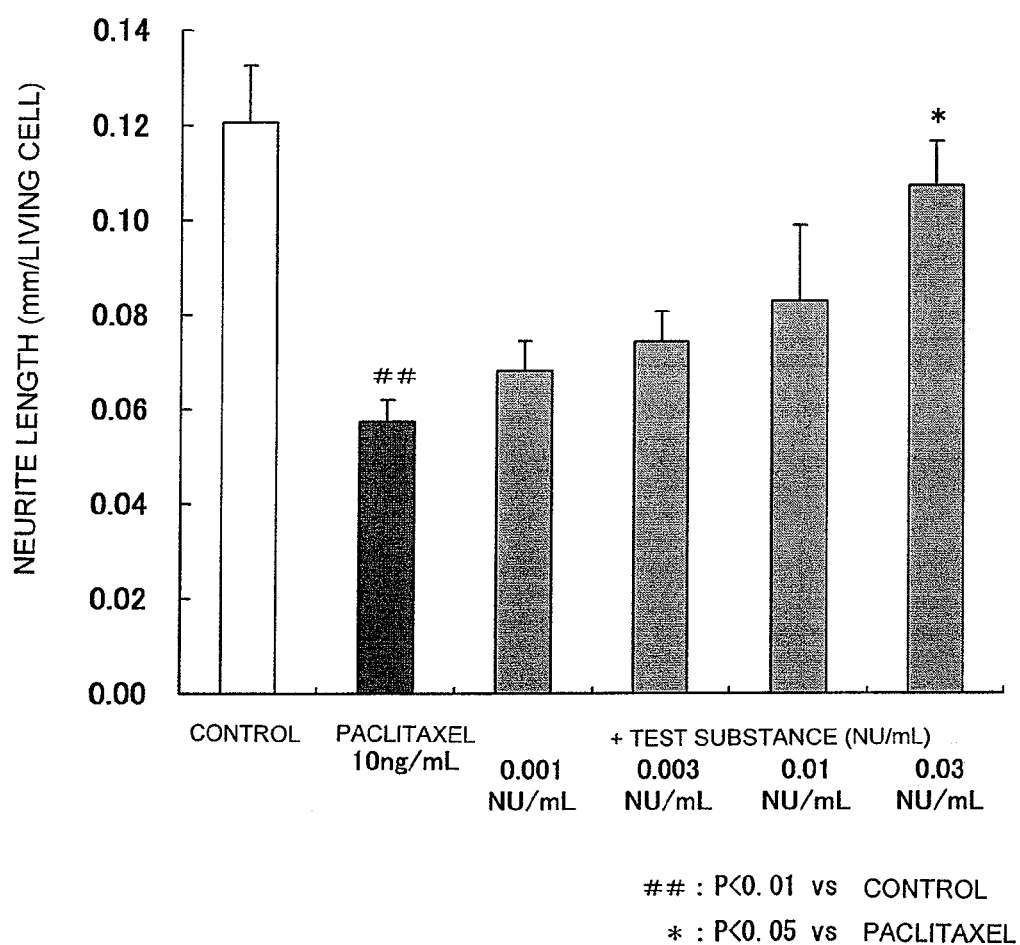
FIG. 4 is an experimental result using DRG cells on suppressive effect of the extract from inflamed tissues inoculated with vaccinia virus of the present invention on the neurite outgrowth inhibition induced by paclitaxel.

An example of the test results is shown in FIGS. 3 and 4. It was revealed that, in both of the PC12 cells and the DRG cells, the neurite outgrowth was inhibited by paclitaxel, but in contrast, the combination treatment with the extract of the present invention significantly suppressed the neurite outgrowth inhibition depending on the concentration. In particular, the above effect was observed in the DRG cells as nerve cells. Therefore, it is suggested that one of the action mechanisms of the alleviation effect of the extract of the present invention on the peripheral nerve disorder is the suppression of the disorder in neurite outgrowth.

Pharmacological Test 3

Effect on Rat Peripheral Nerve Disorder Induced by Oxaliplatin

In the similar manner as in Pharmacological Test 1, the effect of the extract of the present invention (the extract from inflamed skins of rabbits inoculated with vaccinia virus produced in Example 1) was examined on hyperesthesia such as allodynia by mechanical stimuli and paresthesia in low temperature stimuli induced by the administration of oxaliplatin, a platinum drug. Oxaliplatin is the medicinal agent most frequently causing peripheral nerve disorders, and it is highly desirable to develop methods for preventing and improving the disorders.

(1) Administration of Test Substance

In the similar manner as in Pharmacological Test 1, rats were separated into three groups of a control group, group administered with oxaliplatin and group administered with oxaliplatin and the test substance (group administered with oxaliplatin+test substance). Oxaliplatin (100 mg of freeze-dried formulation) was dissolved in 5% dextrose in water to be used. To the group administered with oxaliplatin, oxaliplatin (4 mg/kg) was intraperitoneally administered twice (on two consecutive days) per week for 4 weeks, that is, in a total of 8 times. To the group administered with oxaliplatin+test substance, the test substance (200 NU/kg) was orally administered three times a week, that is, on the starting day and the second and the third days of the oxaliplatin administration. The test substance was administered just before the administration of oxaliplatin, and the administration was continued for 4 weeks, that is, in a total of 12 times. To the control group, the solvent (5% dextrose in water) used in the oxaliplatin administration was similarly administered (1 mL/kg).

(2) Von Frey Test

In the similar manner as in Pharmacological Test 1 (2), every week, on day 6 from the start of the oxaliplatin administration, von Frey test was carried out to examine the effect of the test substance on allodynia.

Figure 5:
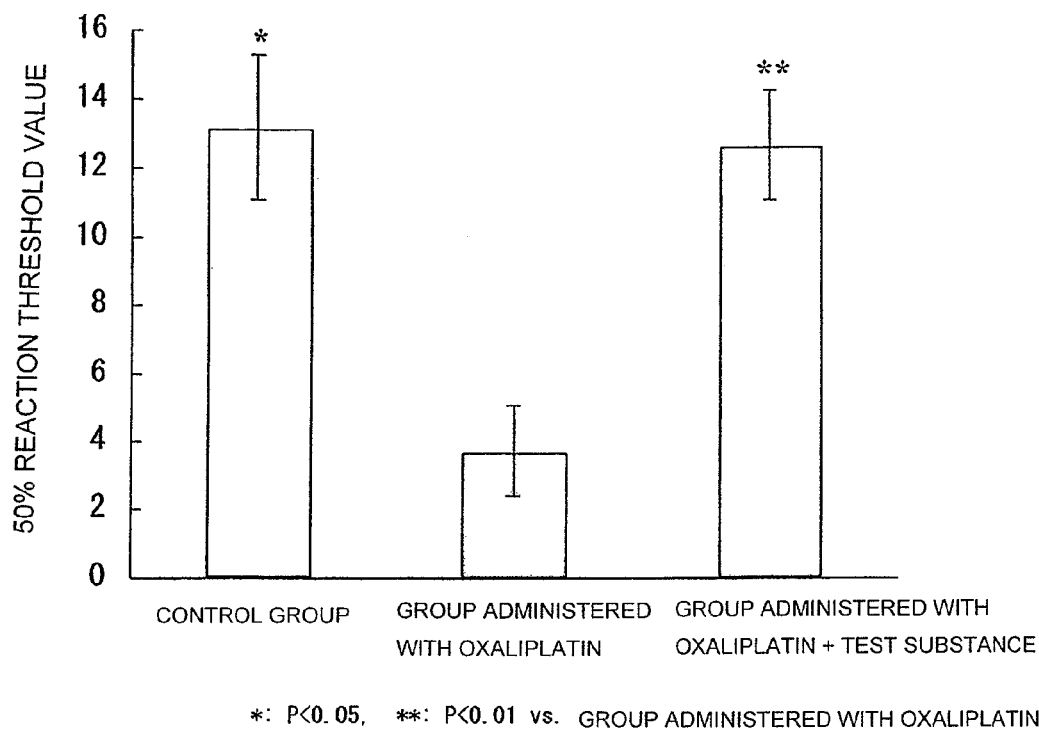
FIG. 5 is an experimental result of the von Frey test on alleviation effect of the extract from inflamed tissues inoculated with vaccinia virus of the present invention on the hyperesthesia induced by oxaliplatin.

An example of the test results (the second week) is shown in FIG. 5. In the second week of the test, in the group administered with oxaliplatin, the 50% reaction threshold value was remarkably lowered as compared with the control group. In contrast, in the group administered with oxaliplatin+test substance in which oxaliplatin was administered in combination with the extract of the present invention, 50% reaction threshold value substantially the same as in the control group was shown, and lowering the 50% reaction threshold value was significantly inhibited in comparison with the group administered with oxaliplatin. From the results, the extract of the present invention was ascertained to have an excellent prevention or improvement effect on the hyperesthesia induced by oxaliplatin.

(3) Cold Plate Test

Cold plate test was carried out on day 5 after starting the oxaliplatin administration to examine the effect of the test substance on paresthesia in low temperature stimuli. On the day before the test, each of the rats in three groups in (1) was placed on a cold plate (Hot/Cold plate Cat. No. 35100, manufactured by Ugo Basile Biological Research Apparatus) for 30 minutes to be sufficiently acclimated. On the day of the test, the rat was placed on the cold plate at 4° C. Then, the behavior of the rat was observed for 150 seconds and the reaction time to posterior foot avoidance (latent time) was measured. In order to eliminate observer bias, the behavior observation was carried out under the condition where the drug administered to each rat group was not known. The test was carried out three times and the results were averaged. Then, the mean value and standard error were calculated. Multiple comparisons between groups were, after one-way analysis of variance (one-way ANOVA), carried out by the comparisons between each group in the similar manner as in the other pharmacological tests according to the Tukey-Kramer method. Stat View (Abacus Concepts, Berkely, Calif., USA) was used for a significance test, and a significance level of less than 5% ($p<0.05$) was considered as a significant difference.

Figure 6:
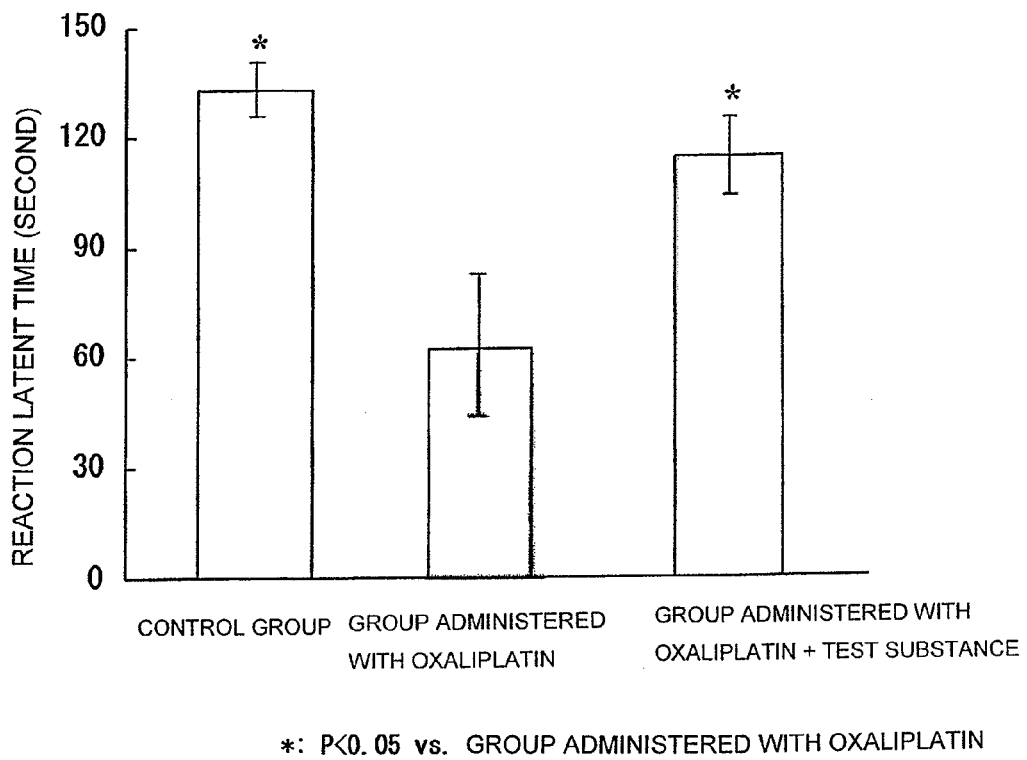
FIG. 6 is an experimental result of the cold plate test on alleviation effect of the extract from inflamed tissues inoculated with vaccinia virus of the present invention on the hyperesthesia induced by oxaliplatin.

An example of the test results (the second week) is shown in FIG. 6. In the second week of the above test, with respect to the cold stimuli by the cold plate, in the group administered with oxaliplatin, the latent time was remarkably shortened, but in the group administered with oxaliplatin+test substance, the latent time was recovered substantially the same level as that in the control group. From the above results, the extract of the present invention was ascertained to have an excellent effect on the paresthesia (hypersensitivity to cold stimuli) induced by oxaliplatin. In the same manner as in paclitaxel, examples of the characteristic symptom of a peripheral nerve disorder induced by oxaliplatin include hypersensitivity with respect to cold stimuli. In the same manner as in the result of acetone test in Pharmacological Test 1 (3), the test (cold plate test) reflects the symptom, and thus the result shows an excellent prevention or improvement effect of the extract of the present invention on the hyperesthesia induced by anti-cancer agents.

INDUSTRIAL APPLICABILITY

As apparent from the results of Pharmacological Tests, it was revealed that the extract from inflamed tissues inoculated with vaccinia virus of the present invention has an excellent prevention or alleviation effect on the peripheral nerve disorder in the rat oral administration tests in which the hyperesthesia such as allodynia induced by mechanical stimuli and the paresthesia in low temperature stimuli induced by the administration of an anti-cancer agent such as paclitaxel or oxaliplatin were used as indexes of the peripheral nerve disorder. In addition, the extract from inflamed tissues inoculated with vaccinia virus of the present invention has a remarkable inhibitory effect in the in vitro test on the neurite outgrowth inhibition induced by paclitaxel. Therefore, it was revealed that the extract from inflamed tissues inoculated with vaccinia virus of the present invention is effective against the peripheral nerve disorder induced by the administration of the anti-cancer agent such as paclitaxel or oxaliplatin. The commercially available preparation of the extracted solution from inflamed skins of rabbits inoculated with vaccinia virus has been used for many years and considered as a remarkably highly safe medicinal agent. In this manner, the extract from inflamed tissues inoculated with vaccinia virus of the present invention is effective as the prophylactic or alleviating agent for nerve disorders in the peripheral nervous system, for example, paresthesia such as numbness of limb extremities and hyperesthesia such as pains that are induced by an anti-cancer agent and is a highly safe and remarkably highly useful medicinal agent with few side effects.

The invention claimed is:

1. A drug system comprising a combination of an anti-cancer agent which causes axonal degeneration, axonopathy or damage to microtubules in axons, and a prophylactic or alleviating agent for a peripheral nerve disorder induced by the anti-cancer agent, the prophylactic or alleviating agent comprising, as an active ingredient, an extract from an inflamed tissue inoculated with vaccinia virus which alleviates the peripheral nerve disorder caused by axonal degeneration, axonopathy, or damage to microtubules in the axons caused by the anti-cancer agent.

2. The drug system according to claim 1, wherein the anti-cancer agent is a microtubule inhibitor and the extract alleviates the peripheral nerve disorder caused by the anti-cancer agent by suppression of disorder in neurite outgrowth.

3. The drug system according to claim 2, wherein the microtubule inhibitor is a taxane drug.

4. The drug system according to claim 3, wherein the taxane drug is paclitaxel or docetaxel.

5. The drug system according to claim 3, wherein the taxane drug is paclitaxel.

6. The drug system according to claim 2, wherein the microtubule inhibitor is a vinca alkaloid drug.

7. The drug system according to claim 1, wherein the anti-cancer agent is a platinum drug, and the extract alleviates the peripheral nerve disorder caused by axonopathy caused by the anti-cancer agent.

8. The drug system according to claim 7, wherein the platinum drug is oxaliplatin, carboplatin, cisplatin or nedaplatin.

9. The drug system according to claim 7, wherein the platinum drug is oxaliplatin.

10. The drug system according to claim 1, wherein the peripheral nerve disorder induced by the anti-cancer agent is acute or chronic pain, numbness, paresthesia, hyperesthesia or dysesthesia.

11. The drug system according to claim 1, wherein the inflamed tissue is a rabbit skin tissue.

12. The drug system according to claim 1, wherein the prophylactic or alleviating agent is an oral preparation.

13. The drug system according to claim 1, wherein the prophylactic or alleviating agent is an injectable preparation.

14. A drug system as claimed in claim 1 wherein the prophylactic or alleviating agent and the anti-cancer agent are separate from each other.

15. A drug system as claimed in claim 1 wherein the prophylactic or alleviating agent and the anti-cancer agent are administered together.

16. A drug system as claimed in claim 1 wherein the prophylactic or alleviating agent and the anti-cancer agent are administered sequentially.

17. A method for treating a peripheral nerve disorder induced by an anti-cancer agent which causes axonal degeneration, axonopathy or damage to microtubules in axons, comprising administering to a patient in need of such treatment a prophylactic or alleviating agent comprising, as an active ingredient, an extract from an inflamed tissue inoculated with vaccinia virus which alleviates the peripheral nerve disorder caused by the axonal degeneration, axonopathy, or damage to microtubules in the axons caused by the anti-cancer agent.

18. A method for treating a peripheral nerve disorder induced by an anti-cancer agent as claimed in claim 17 wherein the anti-cancer agent is a microtubule inhibitor.

19. A method for treating a peripheral nerve disorder induced by an anti-cancer agent as claimed in claim 18 wherein the microtubule inhibitor is a taxane drug.

20. A method for treating a peripheral nerve disorder induced by an anti-cancer agent as claimed in claim 19 wherein the taxane drug is paclitaxel or docetaxel.

21. A method for treating a peripheral nerve disorder induced by an anti-cancer agent as claimed in claim 17 wherein the anti-cancer agent is a platinum drug.

22. A method for treating a peripheral nerve disorder induced by an anti-cancer agent as claimed in claim 21 wherein the platinum drug is oxaliplatin, carboplatin, cisplatin or nedaplatin.

23. A method for treating a peripheral nerve disorder induced by an anti-cancer agent as claimed in claim 17 wherein the peripheral nerve disorder induced by an anti-cancer agent is acute or chronic pain, numbness, paresthesia, hyperesthesia or dysesthesia, the inflamed tissue is a rabbit skin tissue, and the prophylactic or alleviating agent is an oral preparation or an injectable preparation.

24. A method for treating a peripheral nerve disorder induced by an anti-cancer agent as claimed in claim 17 wherein the prophylactic or alleviating agent and the anti-cancer agent are administered separate from each other.

25. A method for treating a peripheral nerve disorder induced by an anti-cancer agent as claimed in claim 17 wherein the prophylactic or alleviating agent and the anti-cancer agent are administered together.

26. A method for treating a peripheral nerve disorder induced by an anti-cancer agent as claimed in claim 17 wherein the prophylactic or alleviating agent and the anti-cancer agent are administered sequentially.

* * * * *